United States Patent [19]

Sugiyama

[11] Patent Number: 5,739,329
[45] Date of Patent: Apr. 14, 1998

[54] PROCESS FOR PRODUCING HEXAHYDROPYRIDAZINE AND HEXAHYDROPYRIDAZINE-1,2-DICARBOXY DERIVATIVE

[75] Inventor: Tatsuo Sugiyama, Shizuoka-ken, Japan

[73] Assignee: Ihara Chemical Industry Co., Ltd., Tokyo, Japan

[21] Appl. No.: 530,185

[22] PCT Filed: Feb. 10, 1995

[86] PCT No.: PCT/JP95/00184

§ 371 Date: Oct. 5, 1995

§ 102(e) Date: Oct. 5, 1995

[87] PCT Pub. No.: WO95/21828

PCT Pub. Date: Aug. 17, 1995

[30] Foreign Application Priority Data

Feb. 10, 1994 [JP] Japan ............................ 6-037914
Feb. 10, 1994 [JP] Japan ............................ 6-037915

[51] Int. Cl.⁶ ........................................... C07D 237/04
[52] U.S. Cl. ............................... 544/224; 544/235
[58] Field of Search ............................ 544/224, 235

[56] References Cited

U.S. PATENT DOCUMENTS 2,841,584  7/1958  Hunter ............................ 544/224
5,310,738  5/1994  Nakayama ...................... 544/224

FOREIGN PATENT DOCUMENTS 40785    4/1978  Japan .
92-12136 7/1992  WIPO ............................ 544/224

OTHER PUBLICATIONS

Abstract for JP 4-244067 (Sep. 1, 1992), Nakayama.
English translation of JP 40785 (Apr. 1978).

Primary Examiner—Emily Bernhardt
Attorney, Agent, or Firm—Oblon, Spivak, McClelland, Maier & Neustadt, P.C.

[57] ABSTRACT

The present invention provides a process for producing a hexahydropyridazine-1,2-dicarboxy derivative represented by the general formula:

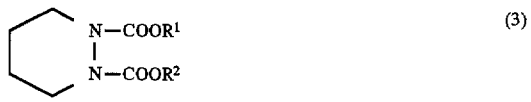

(3)

wherein $R^1$ and $R^2$ represent each independently an alkyl group, by reacting a hydrazinedicarboxy derivative represented by the general formula:

$$R^1OOC-NH-NH-COOR^2 \quad (1)$$

wherein $R^1$ and $R^2$ have the same meaning as mentioned above, with a dihalogenobutane represented by the general formula:

$$X^1-CHCH_2CH_2CH_2-X^2 \quad (2)$$

wherein $X^1$ and $X^2$ represent each independently a halogen atom, in the presence of an alkali metal hydroxide, characterized in that the above reaction is effected in an aprotic polar solvent, and a process for producing a hexahydropyridazine, characterized by decarboxylating the thus obtained hexahydropyridazine-1,2-dicarboxy derivative (3) without isolation in the presence of an alkali metal hydroxide and a hydrogen-denoting compound.

2 Claims, No Drawings

PROCESS FOR PRODUCING HEXAHYDROPYRIDAZINE AND HEXAHYDROPYRIDAZINE-1,2-DICARBOXY DERIVATIVE

TECHNICAL FIELD

The present invention relates to a process for producing a hexahydropyridazine which is useful as an intermediate for benzothiazine type agricultural chemicals (herbicide), and to a process for producing a hexahydropyridazine-1,2-dicarboxy derivative which is useful as an intermediate for producing this hexahydropyridazine.

BACKGROUND ART

The production of hexahydropyridazine has heretofore been carried out by isolating a hexahydropyridazine-1,2-dicarboxy derivative and then decarboxylating the same; however, no process for producing hexahydropyridazine by decarboxylating the hexahydropyridazine-1,2-dicarboxy derivative without isolation has been known.

As a process for producing the above hexahydropyridazine-1,2-dicarboxy derivative, the present inventors have already proposed a process by which a hydrazinedicarboxy derivative represented by the general formula:

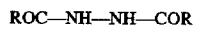

ROC—NH—NH—COR wherein R represents an alkoxy group or an aryl group, is reacted with a 1,4-dihalogenobutane in the presence of a base selected from alkali metal carbonates and hydroxides (see Japanese Patent Application Kokai No. 4-244,067).

However, this process has been unable to obtain the objective compound in a sufficient yield in the case where an alkali metal hydroxide is used as the base for a compound having the above formula for hydrazinedicarboxy derivative in which R represents an alkoxy group.

An object of the present invention is to provide a process for producing hexahydropyridazine simply and cheaply on an industrial scale.

Another object of the present invention is to provide a process for producing a hexahydropyridazine-1,2-dicarboxy derivative which process has solved the above-mentioned problems of prior art.

The present inventor has made extensive research for the purpose of providing a process for producing a hexahydropyridazine-1,2-dicarboxy derivative by which the above-mentioned problems of prior art have been solved, and has, as a result, found that when in a process for producing a hexahydropyridazine-1,2-dicarboxy derivative by reacting a hydrazinedicarboxy derivative with a dihalogenobutane in the presence of an alkali metal hydroxide, said reaction is conducted in an aprotic polar solvent, the problems of prior art can be solved, and further found that the hexahydropyridazine is obtained by such a simple procedure that the thus obtained hexahydropyridazine-1,2-dicarboxy derivative is decarboxylated without isolation using an alkali metal hydroxide. Based on this findings, he has completed the present invention directed to a process for producing hexahydropyridazine simply and cheaply on an industrial scale.

DISCLOSURE OF THE INVENTION

That is to say, the first process of the present invention provides a process for producing a hexahydropyridazine-1,2-dicarboxy derivative represented by the general formula:

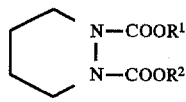

wherein $R^1$ and $R^2$ represent each independently an alkyl group, by reacting a hydrazinedicarboxy derivative represented by the general formula:

$$R^1OOC-NH-NH-COOR^2 \quad (1)$$

wherein $R^1$ and $R^2$ have the same meaning as above, with a dihalogenobutane represented by the general formula:

$$X^1-CH_2CH_2CH_2CH_2-X^2 \quad (2)$$

wherein $X^1$ and $X^2$ represent each independently a halogen atom, in the presence of an alkali metal hydroxide, characterized in that above reaction is effected in an aprotic polar solvent.

The second process of the present invention provides a process for producing hexahydropyridazine, characterized by reacting a hydrazinedicarboxy derivative represented by the general formula:

$$R^1OOC-NH-NH-COOR^2 \quad (1)$$

wherein $R^1$ and $R^2$ represent each independently an alkyl group, with a dihalogenobutane represented by the general formula:

$$X^1-CH_2CH_2CH_2CH_2-X^2 \quad (2)$$

wherein $X^1$ and $X^2$ represent each independently a halogen atom, in the presence of an alkali metal hydroxide in an aprotic polar solvent to obtain a hexahydropyridazine-1,2-dicarboxy derivative represented by the general formula:

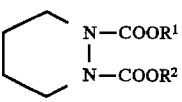

wherein $R^1$ and $R^2$ have the same meaning as above, and decarboxylating this hexahydropyridazine-1,2-dicarboxy derivative without isolation in the presence of an alkali metal hydroxide and a hydrogen-donating compound.

BEST MODE FOR CARRYING OUT THE INVENTION

The present invention is explained in detail below.

In the present invention, first of all, according to the first process of the present invention, the hydrazinedicarboxy derivative (1) is reacted with the dihalogenobutane (2) in the presence of an alkali metal hydroxide in an aprotic polar solvent to obtain a hexahydropyridazine-1,2-dicarboxy derivative (3).

The hydrazinedicarboxy derivative (1) used as a starting material in the first process of the present invention may be a compound of the above formula in which $R^1$ and $R^2$ are each independently an alkyl group, specifically, for example, an alkyl group having 1 to 8 carbon atoms and a straight chain, branched chain or alicyclic structure, more specifically such an alkyl group as a methyl group, an ethyl group, a propyl group, an isopropyl group, a butyl group, a pentyl group, a hexyl group, a cyclohexyl group, a heptyl group, an octyl group or the like. As such compounds, specifically, for example, dimethyl hydrazinedicarboxylate, diethyl hydrazinedicarboxylate, dibutyl hydrazinedicarboxylate and the like can be mentioned as examples. However, hydrazinedicarboxy derivatives (1) having substituents corresponding to the structure of the objective hexahydropyridazine-1,2-dicarboxy derivative (3) may be appropriately selected. Incidentally, compounds in which $R^1$ and $R^2$ are the same substituent, are easily available as the starting material.

The dihalogenobutane (2) used as a starting material in the first process of the present invention may be a compound of the formula wherein $X^1$ and $X^2$ are each independently a halogen atom, specifically a chlorine, a bromine, a fluorine or an iodine atom. In particular, compounds of the formula in which they are chlorine atoms or bromine atoms are easily available as the starting material and hence suitable. As such compounds, 1,4-dichlorobutane, 1,4-dibromobutane, 1-bromo-4-chlorobutane and the like can be mentioned as examples. Incidentally, this dihalogenobutane (2) may, if desired, be used in admixture of two or more.

Moreover, as the alkali metal hydroxide used in the first process of the present invention, those which are usually so called may be used and, for example, sodium hydroxide and potassium hydroxide can be mentioned as examples.

In the reaction in the first process of the present invention, as the mole ratio of the hydrazinedicarboxy derivative (1), the dihalogenobutane (2) and the alkali metal hydroxide used, a range of 1:(1–10):(1–20), preferably 1:(1–2):(2–4) can be mentioned as an example.

In the first process of the present invention, an aprotic polar solvent is used as the reaction solvent. As this aprotic polar solvent, those which are usually called as aprotic polar solvents may be used, and specifically, there can be mentioned, for example, amide type aprotic polar solvents, representatives of which are N,N-dimethylformamide (DMF), N,N-dimethylacetamide (DMAc), N,N-diethylacetamide (DEAc) and the like; sulfur atom-containing aprotic polar solvents, representatives of which are tetrahydrothiophene-1,1-dioxide (sulfolane), N,N-dimethyl sulfoxide (DMSO) and the like; and others such as 1,3-dimethylimidazolidinone (DMI), N,N-dimethyl propyleneurea (DMPU) and the like. These aprotic polar solvents may be used, if necessary, in admixture of two or more. The amount of the aprotic polar solvent used may be at least such an amount that stirring is possible; however, usually an amount of 500 to 2,000 ml per mole of the hydrazinedicarboxy derivative (1) is suitable.

The reaction in the first process of the present invention is effected in a temperature range of from 10° C. to 80° C., preferably from 40° C. to 70° C., usually under atmospheric pressure, and the reaction time is usually 30 minutes to 24 hours, preferably 1 to 5 hours. This reaction may be effected in the co-existence of a compound capable of functioning as a phase transfer catalyst such as a quaternary phosphonium salt, a quaternary ammonium salt, a crown ether, a polyethylene glycol or the like.

Incidentally, the hydrazinedicarboxy derivative (1) used as the starting material in the first process of the present invention can be easily obtained by the method stated in Organic Synthesis Coll., Vol. III, 375.

In the present invention, according to the second process of the present invention, the hexahydropyridazine-1,2-dicarboxy derivative (3) obtained by reacting the hydrazinedicarboxy derivative (1), the dihalogenobutane (2) and an alkali metal hydroxide as mentioned above in the presence of an aprotic polar solvent is subsequently decarboxylated without isolation in the presence of an alkali metal hydroxide and a hydrogen-donating compound to produce hexahydropyridazine.

The alkali metal hydroxide used in the second process of the present invention maybe the same as used in the reaction of the first process of the present invention and specifically sodium hydroxide and potassium hydroxide can be mentioned as examples. The alkali metal hydroxide used here may be different from those used in the reaction for producing the above hexahydropyridazine-1,2-dicarboxy derivative (3).

As the hydrogen-donating compound used in the second process of the present invention, there can be mentioned, for example, compounds having a hydroxyl group, more specifically, water; alcohols having 1 to 6 carbon atoms and a straight chain, branched chain or ring structure such as methanol, ethanol, n-propanol, i-propanol, n-butanol, i-butanol, n-pentanol, i-pentanol, n-hexanol, cyclohexanol and the like; etc. In general, water is preferably used because it is easily available and can easily be handled.

The amounts of the alkali metal hydroxide and hydrogen-donating compound used in the second process of the present invention may be such that the mole ratio of the hydrazinedicarboxy derivative (1) used in the prior reaction: the alkali metal hydroxide: the hydrogen-donating compound is in a range of 1:(2–20):(2–20), preferably 1:(4–8):(2–8).

In the second process of the present invention, the reaction mixture obtained in the reaction for producing the hexahydropyridazine-1,2-dicarboxy derivative (3) is used, so that usually, it is not particularly necessary to add a solvent. However, if desired, there may be added an aprotic polar solvent, specifically an amide type aprotic polar solvent, representatives of which are N,N-dimethylformamide (DMF), N,N-dimethylacetamide (DMAc), N, N-diethylacetamide (DEAc) and the like; a sulfur atom-containing aprotic polar solvent, representatives of which are tetrahydrothiophene-1,1-dioxide (sulfolane), N,N-dimethyl sulfoxide (DMSO) and the like; or others such as 1,3-dimethylimidazolidinone (DMI), N,N-dimethylpropyleneurea (DMPU) and the like. When an aprotic polar solvent is added, the aprotic polar solvent to be added may be the same as or different from that used in the reaction for the production of the above hexahydropyridazine-1,2-dicarboxy derivative (3). The amount of the solvent added may be at least such an amount that the reaction system can be stirred; however, it is suitable to adjust the total solvent amount to fall in the range of from 500 ml to 2,000 ml per mole of the hydrazinedicarboxy derivative (1) used in the reaction for producing the hexahydropyridazine-1,2-dicarboxy derivative (3).

The reaction in the second process of the present invention is carried out in a temperature range of from 80° C. to 160° C., preferably from 90° C. to 120° C., usually under atmospheric pressure; however, the reaction maybe effected under pressure. The reaction time is 1 to 24 hours, preferably 2 to 8 hours.

Incidentally, when the isolated hexahydropyridazine-1,2-dicarboxy derivative (3) was used and subjected to decarboxylation in the presence of an alkali metal hydroxide and a hydrogen-donating compound in an aprotic polar solvent, the production of the hexahydropyridazine which was the objective compound of the present process was not confirmed.

The present invention is specifically explained below referring to Examples and Comparative Examples.

EXAMPLE 1

Production (1) of diethyl hexahydropyridazine-1,2-dicarboxylate

Into a 500-ml, four-necked flask equipped with a reflux condenser, a stirrer and a thermometer were charged 35.2 g (0.2 mole) of diethyl hydrazinedicarboxylate, 25.9 g (0.204 mole) of 1,4-dichlorobutane, 200 ml of 1,3-dimethylimidazolidinone and 22.4 g (0.4 mole) of potassium hydroxide, gradually warmed up to 50°–60° C. and aged for 3 hours. After completion of the reaction, the reaction mixture was cooled and filtered to remove the solid matters, after which the solvent was removed by distillation under reduced pressure. The residue obtained was distilled under reduced pressure (110° C./1 mmHg) to obtain 33.0 g of diethyl hexahydropyridazine-1,2-dicarboxylate. The yield was 72%.

EXAMPLE 2

Production (2) of diethyl hexahydropyridazine-1,2-dicarboxylate

The same procedure as in Example 1 was carried out, except that 200 ml of N,N-dimethylformamide was substituted for the 200 ml of 1,3-dimethylimidazolidinone. As a result, 27.6 g of diethyl hexahydropyridazine-1,2-dicarboxylate was obtained. The yield was 60%.

EXAMPLE 3

Production (1) of hexahydropyridazine

Into a four-necked flask equipped with a reflux condenser, a stirrer and a thermometer were charged 176 g (1.0 mole) of diethyl hydrazinedicarboxylate, 129.5 g (1.02 moles) of 1,4-dichlorobutane, 1 liter of 1,3-dimethylimidazolidinone and 112.4 g (2.0 moles) of potassium hydroxide, gradually warmed up to 50° C.–60° C., and then subjected to reaction for 3 hours in this temperature range. After the reaction, the reaction mixture was cooled and filtered. To the filtrate obtained were added 224.4 g (4.0 moles) of potassium hydroxide and 72 g (4.0 moles) of water and the temperature was elevated to 100° C.–110° C., after which the mixture was aged in the same temperature range for 4 hours, cooled and filtered to remove the inorganic salt. The filtrate was rectified to obtain 53 g of hexahydropyridazine having a boiling point of 38° C./8 mmHg. The yield was 61.6%.

EXAMPLE 4

Production (2) of hexahydropyridazine

The same procedure as in Example 3 was carried out, except that 1 liter of N,N-dimethylpropyleneurea was substituted for the 1 litter of 1,3-dimethylimidazolidinone. As a result, 44.5 g of hexahydropyridazine was obtained. The yield was 51.7%.

EXAMPLE 5

Production (3) of hexahydropyridazine

Into a four-necked flask equipped with a reflux condenser, a stirrer and a thermometer were charged 176 g (1.0 mole) of diethyl hydrazinedicarboxylate, 129.5 g (1.02 moles) of 1,4-dichlorobutane, 2 liters of N,N-dimethylformamide and 112.4 g (2.0 moles) of potassium hydroxide, gradually warmed up to 50°–60° C. and subjected to reaction for 3 hours in this temperature range. After the reaction, the reaction mixture was cooled and filtered, after which 336.6 g (6.0 moles) of potassium hydroxide and 108 g (6.0 moles) of water were added to the filtrate obtained. The temperature was elevated to 100°–110° C. and stirring was continued for 4 hours in this temperature range, after which the mixture was cooled and filtered to remove the inorganic salt. The filtrate was rectified to obtain 52 g (yield: 60.5% ) of hexahydropyridazine having a boiling point of 38° C./8 mmHg.

EXAMPLE 6

Production (4) of hexahydropyridazine

Into a four-necked flask equipped with a reflux condenser, a stirrer and a thermometer were charged 176 g (1.0 mole) of diethyl hydrazinedicarboxylate, 129.5 g (1.02 moles) of 1,4-dichlorobutane, 1 litter of tetrahydrothiophene-1,1-dioxide (sulfolane) and 112.4 g (2.0 moles) of potassium hydroxide, gradually warmed up to 50°–60° C., and subjected to reaction for 3 hours in this temperature range. After the reaction, the reaction mixture was cooled and filtered, and to the filtrate obtained were added 224.4 g (4.0 moles) and 72 g (4.0 moles) of water. The temperature was elevated to 100°–110° C. and stirring was continued for 4 hours in this temperature range, after which the mixture was cooled and filtered to remove the inorganic salt. The filtrate was rectified to obtain 50 g (yield: 58.1%) of hexahydropyridazine having a boiling point of 38° C./8 mmHg.

COMPARATIVE EXAMPLE 1

Decarboxylation of isolated diethylhexahydropyridazine-1,2-dicarboxylate

Into a 100-ml, four-necked flask equipped with a reflux condenser, a stirrer and a thermometer were charged 50 ml of 1,3-dimethylimidazolidinone, 5.75 g (0.025 mole) of diethyl hexahydropyridazine-1,2-dicarboxylate [produced according to the method of (Example 1), isolated and purified], 5.61 g (0.1 mole) of potassium hydroxide and 0.9 g (0.05 mole) of water and stirred for 1.5 hours in a temperature range of 100°–110° C. At this stage, the reaction mixture was analyzed. The objective hexahydropyridazine was not detected. In this analysis, the peak of the diethyl hexahydropyridazine-1,2-dicarboxylate added as a starting material has disappeared.

INDUSTRIAL APPLICABILITY

According to the first process of the present invention, unlike the conventional process, even when such a compound that $R^1$ and $R^2$ in the formula for hydrazinedicarboxy derivative (1) are alkyl groups and a dihalogenobutane (2) are used as the starting materials and an alkali metal hydroxide is used as a base, it has become possible to produce a hexahydropyridazine-1,2-dicarboxy derivative (3) simply and cheaply on a commercial scale.

Also, according to the second process of the present invention, hexahydropyridazine can be produced by such a simple procedure that the hexahydropyridazine-1,2-dicarboxy derivative (3) produced from the hydrazinedicarboxy derivative (1) and the dihalogenobutane (2) is subjected, without isolation, to decarboxylation. Accordingly, in view of simplicity of operation, not only is it suitable for the production of hexahydropyridazine on a industrial scale, but also is it important as a process for producing a useful intermediate for a benzothiazine type herbicide (see Japanese Patent Application Kokai No. 63-264,489).

I claim:

1. A process for producing hexahydropyridazine, comprising reacting a hydrazinedicarboxy compound represented by the formula:

wherein $R^1$ and $R^2$ represent each independently an alkyl group, with a dihalogenobutane represented by the formula:

wherein $X^1$ and $X^2$ represent each independently a halogen atom, in the presence of alkali metal hydroxide in an aprotic polar solvent to obtain a hexahydropyridazine-1,2-dicarboxy compound represented by the formula:

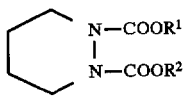

wherein $R^1$ and $R^2$ have the same meaning as defined above, and decarboxylating this hexahydropyridazine-1,2-dicarboxy compound without isolation in the presence of an alkali metal hydroxide and a hydrogen-donating compound selected from the group consisting of water and $C_1$–$C_6$ alcohols.

2. The process according to claim 1, wherein in the compound of formula (1) $R^1$ and $R^2$ are ethyl.

* * * * *